US010685220B2

(12) United States Patent
Lai et al.

(10) Patent No.: US 10,685,220 B2
(45) Date of Patent: Jun. 16, 2020

(54) IMAGE DETECTION METHOD AND IMAGE DETECTION DEVICE FOR DETERMINING POSTURE OF A USER

(71) Applicant: Wistron Corp., New Taipei (TW)

(72) Inventors: Yu-Ren Lai, New Taipei (TW); Po Chun Chen, New Taipei (TW); Ching-An Cho, New Taipei (TW); Kuo Ting Huang, New Taipei (TW); Yu-Yen Chen, New Taipei (TW)

(73) Assignee: Wistron Corp., New Taipei (TW)

( * ) Notice: Subject to any disclaimer, the term of this patent is extended or adjusted under 35 U.S.C. 154(b) by 232 days.

(21) Appl. No.: 15/904,237

(22) Filed: Feb. 23, 2018

(65) Prior Publication Data

US 2019/0122038 A1  Apr. 25, 2019

(30) Foreign Application Priority Data

Oct. 23, 2017  (TW) .............................. 106136329 A

(51) Int. Cl.
*G06K 9/00* (2006.01)
*G06K 9/32* (2006.01)
*A61B 5/00* (2006.01)
*A61B 5/11* (2006.01)
*G06T 7/00* (2017.01)

(52) U.S. Cl.
CPC ........ *G06K 9/00362* (2013.01); *A61B 5/0037* (2013.01); *A61B 5/1116* (2013.01); *A61B 5/4806* (2013.01); *A61B 5/7246* (2013.01); *G06K 9/3233* (2013.01); *A61B 5/1121* (2013.01); *A61B 5/4561* (2013.01); *G06T 7/0014* (2013.01)

(58) Field of Classification Search
None
See application file for complete search history.

(56) References Cited

U.S. PATENT DOCUMENTS

| 2003/0236474 A1 | 12/2003 | Singh |
| 2012/0026308 A1 | 2/2012 | Johnson et al. |
| 2014/0092247 A1 | 4/2014 | Clark et al. |

(Continued)

FOREIGN PATENT DOCUMENTS

| CN | 103347438 A | 10/2013 |
| CN | 205814297 U | 12/2016 |
| CN | 107038402 A | 8/2017 |

(Continued)

OTHER PUBLICATIONS

U.S. Appl. No. 15/920,412 to Chen et al., filed Mar. 13, 2018.

*Primary Examiner* — Atiba O Fitzpatrick

(57) ABSTRACT

An image detection method for determining the posture of a user includes: obtaining a reference image of the user in a region of interest (ROI); obtaining a test image of user at the ROI; executing a feature matching analysis of the test image which compares the feature parameter of the test image and the feature parameter of the reference image to determine the similarity information of the test image and the reference image; and executing a pixel distribution analysis of the test image to obtain user pixel distribution information; and determining the posture of the user based on the user similarity information and the user pixel distribution information.

13 Claims, 9 Drawing Sheets

(56) References Cited

U.S. PATENT DOCUMENTS

2014/0163424 A1* 6/2014 Kawaguchi .......... A61B 5/0077
600/595
2019/0130178 A1* 5/2019 Yamada ............... G06K 9/6255

FOREIGN PATENT DOCUMENTS

| TW | 200607350 A | 2/2006 |
| TW | M468728 U | 12/2013 |
| TW | I469765 B | 1/2015 |
| TW | I478695 B | 4/2015 |

* cited by examiner

IMAGE DETECTION METHOD AND IMAGE DETECTION DEVICE FOR DETERMINING POSTURE OF A USER

CROSS REFERENCE TO RELATED APPLICATIONS

This Application claims priority of Taiwan Patent Application No. 106136329 filed on Oct. 23, 2017, the entirety of which is incorporated by reference herein.

BACKGROUND OF THE INVENTION

Field of the Invention

The disclosure generally relates to an image detection method and an image detection device, and more particularly, to an image detection method and an image detection device for determining the posture of a user.

Description of the Related Art

Image detection technology can be utilized to determine the various postures of a user, such as the sleeping posture of an old person, in order to help care for the old person. Although the facial features of a user may be used to determine sleeping posture, the facial features of a user are quite unstable. The central portion of the face has more features, which result in a higher detection rate, and the side portion of the face has fewer features, which results in a lower detection rate. If the face of the user is almost completely covered, it becomes very hard to detect. Therefore, an image detection method and an image detection device are needed to improve the identification rate and the detection efficiency.

BRIEF SUMMARY OF THE INVENTION

In order to solve the aforementioned problem, the invention proposes an image detection method and an image detection device. In embodiments of the present invention, a body feature such as the trunk or a limb of user is selected as the feature parameter for matching and analysis, and the pixel accumulation value of the user sketch is calculated to perform a pixel distribution analysis. Even if the face of the user cannot be identified, the sleeping posture of the user can be precisely determined based on the above body features, in order to help take care of the user.

In one embodiment of the invention, an image detection method for determining the posture of a user is provided. The image detection method includes obtaining a reference image of the user in a region of interest (ROI); obtaining a test image of the user in the ROI; executing a feature matching analysis of a feature parameter of the test image and a feature parameter of the reference image to obtain user similarity information of the test image and the reference image; executing a pixel distribution analysis for the test image to obtain user pixel distribution information; and determining the posture of the user according to the user similarity information and the user pixel distribution information.

The pixel distribution analysis is utilized to accumulate pixels for a user sketch of the test image along a first direction to obtain the user pixel distribution information. The test image is different from the reference image. The reference image is determined based on whether the pixel difference derived from subtracting two images is smaller than a predetermined value or not. The ROI is a bed on which the user is lying, and the feature parameter comprises any one of the limbs, any one of the facial features, the trunk of the user, or a specific figure of a piece of clothing worn by the user. The similarity information of the feature parameter of the test image and the feature parameter of the reference image is calculated to determine whether it is greater than a first predetermined value or not, and the pixel distribution analysis is utilized to calculate a pixel accumulation value of the user sketch along the first direction respectively based on a sequence along a second direction, and whether the user pixel distribution information of the pixel accumulation value is greater than a second predetermined value or not. The first direction extends from the head of the user to the foot of the user, and the second direction is different from the first direction. In one embodiment, the second direction is vertical to the first direction.

When the similarity information is greater than the first predetermined value and the user pixel distribution information is greater than the second predetermined value, it is determined that the user is in the supine position; and when the similarity information is greater than the first predetermined value and the user pixel distribution information is smaller than or equal to the second predetermined value, it is determined that the user is in a lateral recumbent position. When the similarity information is smaller than or equal to the first predetermined value and the user pixel distribution information is greater than the second predetermined value, it is determined that the user is in the prone position; and when the similarity information is smaller than the first predetermined value and the user pixel distribution information is smaller than or equal to the second predetermined value, it is determined that the user is in a lateral recumbent position.

In another embodiment of the invention, an image detection device is provided. The image detection device includes a sensor and a processor. The sensor is configured to detect a test image and a reference image of a user in a ROI. The processor includes a feature matching module and a determination module. The feature matching module is configured to execute a feature matching analysis of a feature parameter of the test image and a feature parameter of the reference image to obtain user similarity information of the test image and the reference image, and execute a pixel distribution analysis for the test image to obtain user pixel distribution information. The determination module is configured to determine the posture of the user based on the user similarity information and the user pixel distribution information.

BRIEF DESCRIPTION OF DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

Corresponding numerals and symbols in the different figures generally refer to corresponding parts unless otherwise indicated. The figures are drawn to clearly illustrate the relevant aspects of the embodiments and are not necessarily drawn to scale.

DETAILED DESCRIPTION OF THE INVENTION

Figure 1A:
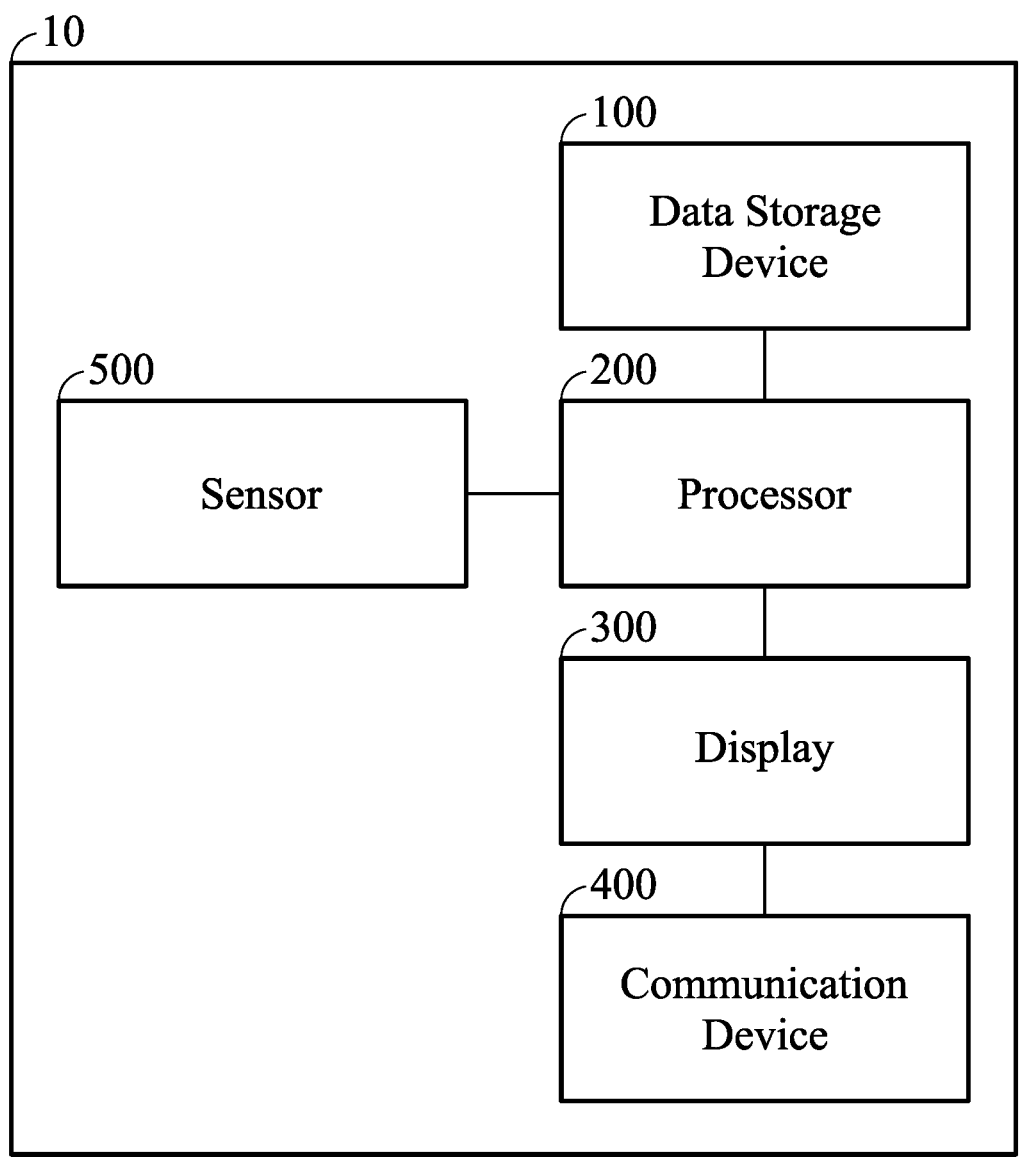
FIG. 1A is a schematic of an image detection device according to an embodiment of the invention.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

FIG. 1A is a schematic of an image detection device according to an embodiment of the invention. The image detection device 10 includes a data storage device 100, a processor 200, a display device 300, a communication device 400, and a sensor 500. The image detection device 10 could be an independent electronic device, or it could be embedded in a mobile electronic device such as a cell phone, a tablet computer, a laptop computer, a gaming apparatus, an electronic book, or a PDA; or it could be an electronic device such as a desktop calculator, a server, a ticket machine, a digital picture frame, a point-of-sale terminal, or a digital map; or it could be any electronic device equipped with a touch module (such as a touch IC). The data storage device 100 includes one or more of the following: a random access memory (RAM), a read-only memory (ROM), a flash memory, a hard disk, a soft disk, a magnetic memory, a compact disc (CD), or a digital video disk (DVD).

In addition, the processor 200 of the image detection device 10 is coupled to the data storage device 100 to access the data in the data storage device 100. The processor 200 may include a digital signal processor (DSP), a microcontroller (MCU), a central-processing unit (CPU) or a plurality of parallel processors relating the parallel processing environment to implement the operating system (OS), firmware, driver and/or other applications of the electronic device. The display device 300 is utilized to display data in the data storage device 100. For example, the display 300 could be a projective display device, a 3D-image display device, an organic LED display, electronic paper, a system-integrated panel, an LED display liquid-crystal panel, or a touch display panel such as a resistive touch panel, a capacitive touch panel, an optical touch panel, or an electromagnetic touch panel. In one embodiment, when the various regular postures of the user have been determined by the processor 200, information about the postures is transmitted to the display 300 by the processor 200 so that the display 300 can display the various postures habitually used by the user.

The communication device 400 supports a wireless communication protocol in order to perform the data transmission with another electronic device. For example, the protocol for wireless communication could constitute GSM, GPRS, EDGE, UMTS, W-CDMA, CDMA2000, TD-CDMA, Bluetooth, NFC, WiFi, WiFi Direct, WiMAX, LTE, LTE-A or TD-LTE. The sensor 500 is utilized to detect the image, sketch or figure of the user. For example, the sensor 500 is an optical sensor which receives an optical signal, transforms the optical signal into an electrical signal, and transmits the electrical signal to the processor 200 for calculation. For example, the sensor 500 may include APS, CMOS image sensor, CCD, infra-red sensor, optical-sensing transistor, or various optical cameras. Therefore, the image of the user could be detected by the sensor 500 even in a dark or twilight environment.

Figure 1B:
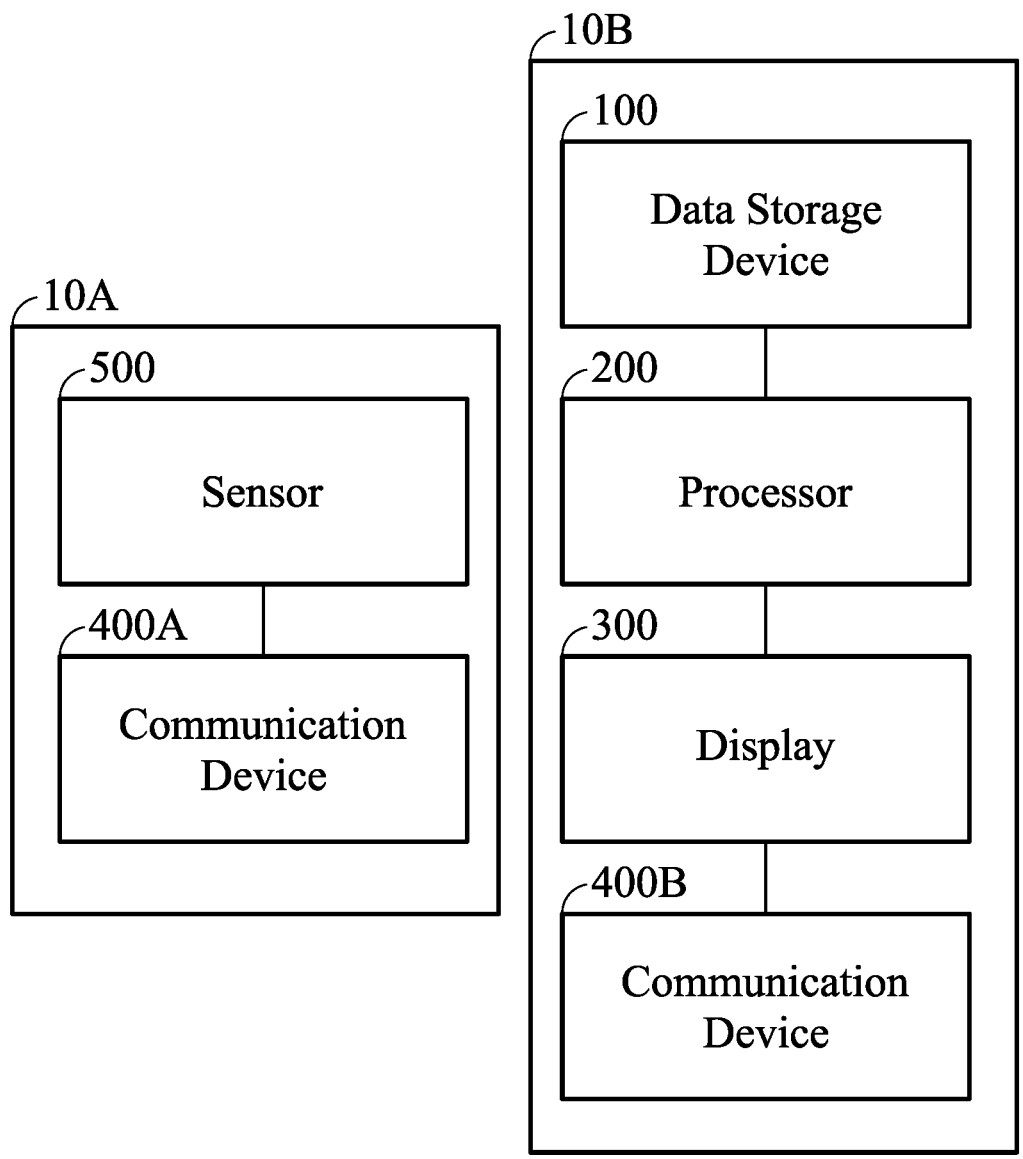
FIG. 1B is a schematic of an image detection device according to another embodiment of the invention.

FIG. 1B is a schematic of an image detection device 10 according to another embodiment of the invention. In the embodiment, the image detection device 10 is designed separately and includes two image detection devices 10A and 10B. The image detection device 10A includes a sensor 500 and a communication device 400A. The image detection device 10B includes a data storage device 100, a processor 200, a display 300 and a communication device 400B. Specifically, the image detection device 10A is installed in the environment of the user, and the image detection device 10B is the main machine. For example, the image detection device 10B could be the server, the large-scale machine or the cloud machine of the manufacture of the image detection device 10. The image detected by the sensor 500 of the image detection device 10A is transmitted to the image detection device 10B through the communication devices 400A and 400B for analysis.

Figure 1C:
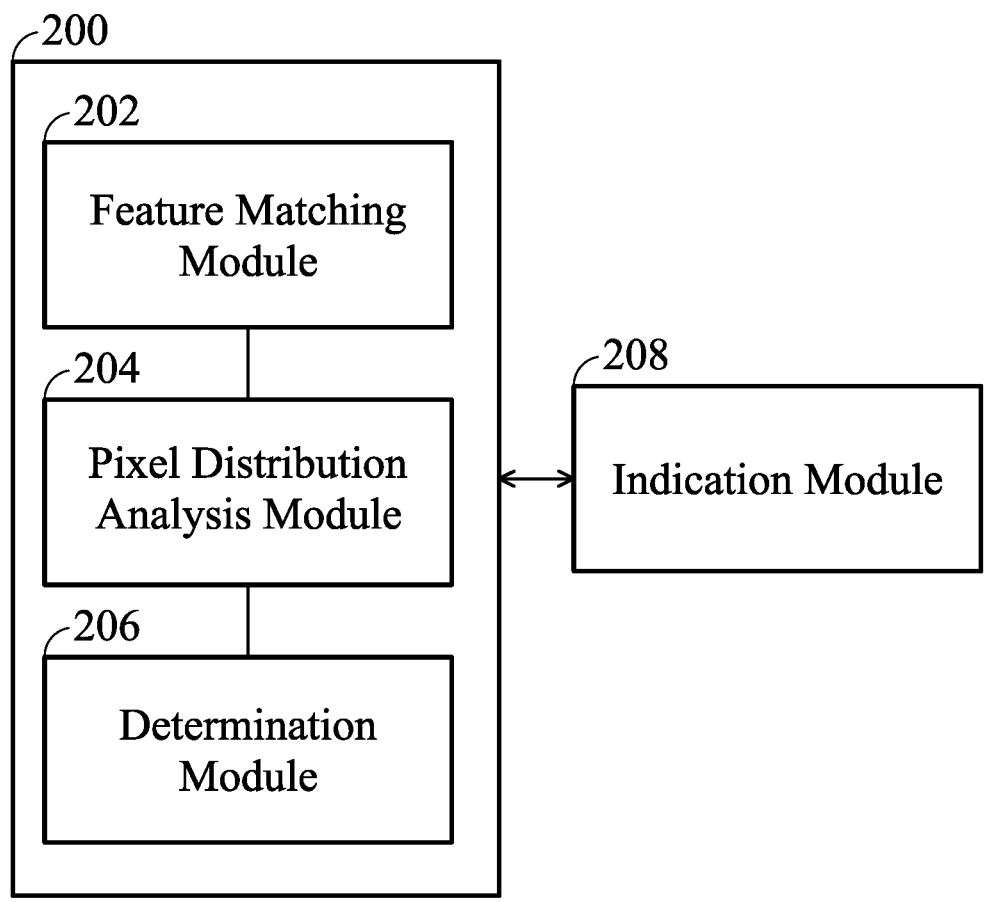
FIG. 1C is a schematic of a processor according to an embodiment of the invention.

FIG. 1C is a schematic of a processor 200 according to an embodiment of the invention. The processor 200 includes a feature matching module 202, a pixel distribution analysis module 204 and a determination module 206. The processor 200 further includes an indication module 208. The feature matching module 202 is utilized to perform the feature matching analysis on the feature parameter of the test image and the feature parameter of the reference image. The pixel distribution analysis module 204 compares the feature parameter of the test image and the feature parameter of the reference image to obtain user similarity information of the test image and the reference image, and executes a pixel distribution analysis of the test image to obtain user pixel distribution information. The determination module 206 determines the postures of the user based on the user similarity information and the user pixel distribution information. The indication module 208 is utilized to generate sound or light to inform other people when the determination module 206 determines that the user is not well, so that the aforementioned other people can take care of the user. For example, the indication module 208 could be an alarm, a buzzer, a warning light, a flash, or an audio signal.

Figure 2:
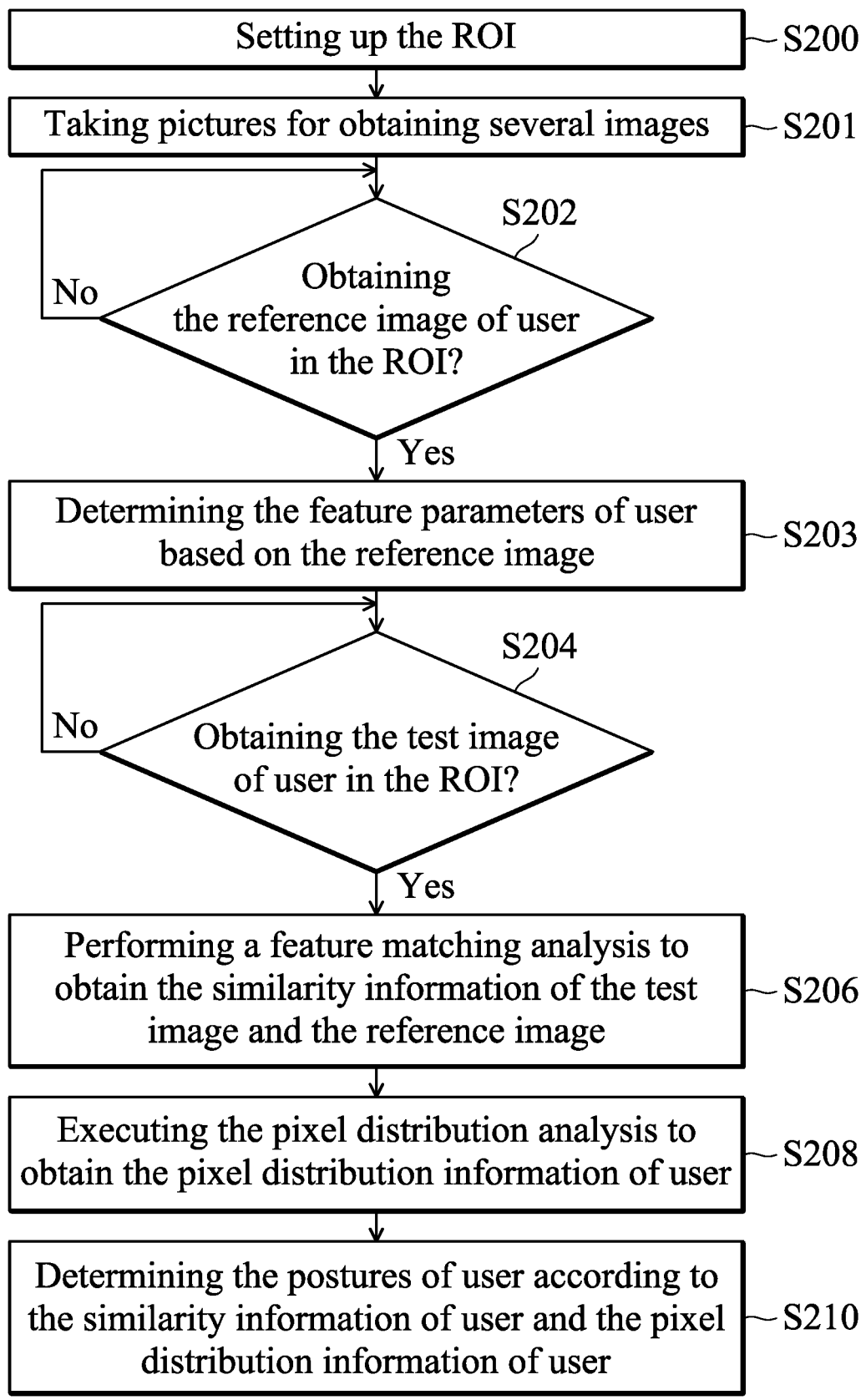
FIG. 2 is a flow chart of an image detection method according to an embodiment of the invention.

FIG. 2 is a flow chart of an image detection method according to an embodiment of the invention. In step S200, the processor 200 sets up the region of interest (ROI) for detection by the image detection device 10. In one embodiment, the image detection device 10 is utilized to determine the sleeping posture of the user. Therefore, the ROI is the bed in which the user sleeps. The ROI could be predetermined by the image detection device 10, or determined by the user based on the environment of the user. When the setting is finished, in step S201, the sensor 500 starts to take pictures and obtains several images of the ROI. For example, the sensor 500 takes 20~60 images per second to record and detect the posture of users in the ROI. The aforementioned number of images per second which are taken by the sensor 500 is merely for illustration, not for limitation. Specifically, the sensor 500 could adjust the number of images per second according to the user's specific environment and the user's specific needs. For example, when the user needs to improve the accuracy of determination, the number of images taken per second by the sensor 500 could be increased.

Afterwards, in step S202, the processor 200 determines whether the reference image of user in the ROI has been obtained or not. Because embodiments of the present invention are mainly utilized for detecting the sleeping posture of a user, it is required to detect a reference image of the user in a motionless state. When the processor 200 detects a first reference image, the first reference image is the matching reference for determining the posture of the user. If the reference image is not obtained, step S202 will be executed. If the reference image is obtained, step S203 will be executed so that the processor 200 determines the feature parameters of the user based on the reference image. In one embodiment, the feature parameter is any one of the limbs, any one of the facial features, the body of the user, or the specific pattern of the clothing worn by the user.

Afterwards, in step S204, the processor 200 determines whether the test image of the user in the ROI has been obtained or not. The above test image is different from the reference image which is a matching reference. In another embodiment, the above test image is identical to the reference image which is a matching reference. If a test image is not obtained, then step S204 will be executed. If the test image is obtained, step S206 will be executed so that the processor 200 performs a feature matching analysis on the test image to compare the feature parameter of the test image and the feature parameter of the reference image for determining the similarity information of the test image and the reference image. The above similarity information is related to the brightness of the user's environment. In a bright environment, it is determined to be similar when 70%~90% of the test images and the reference images are the same. In a dark environment, it is determined to be similar when 30%~50% of the test images and the reference images are the same. In step S208, the processor 200 executes a pixel distribution analysis on the test image to calculate the extension of the sketch of the test image along the first direction for obtaining the user pixel distribution information. The above first direction is defined as the extending direction from the head of the user to the foot of the user. Furthermore, it should be noted that, in the embodiment, the processor 200 executes the feature matching analysis of step S206, and then executes the pixel distribution analysis of step S208. In another embodiment, the processor 200 executes the pixel distribution analysis of step S208, then executes the feature matching analysis of step S206. In another embodiment, the processor 200 simultaneously executes the pixel distribution analysis of step S208 and the feature matching analysis of step S206, which is not limited by the present invention. Finally, in step S210, the postures of the user are determined according to the similarity information of user and the user pixel distribution information.

Figure 3A:
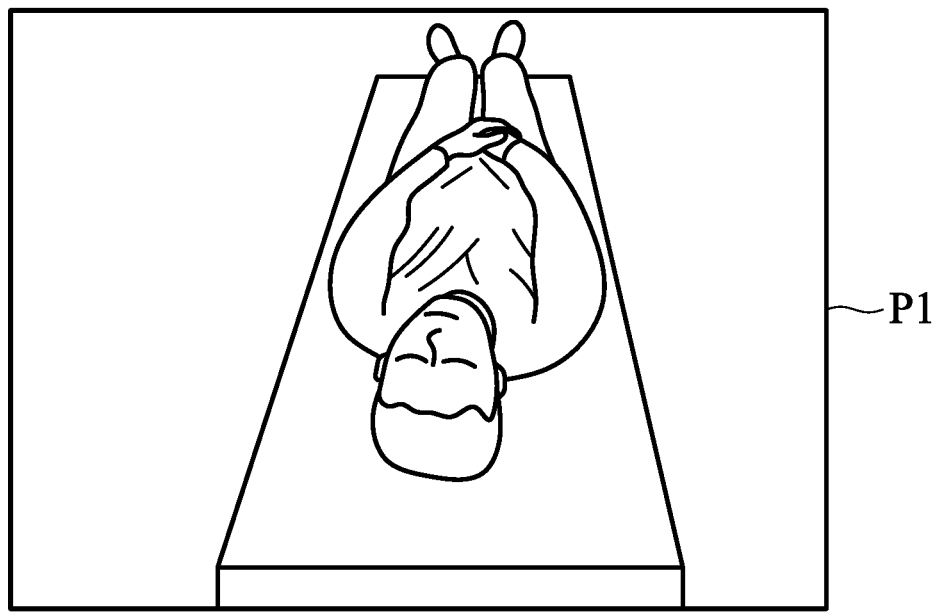
FIG. 3A is a schematic of an image according to an embodiment of the invention.
Figure 3B:
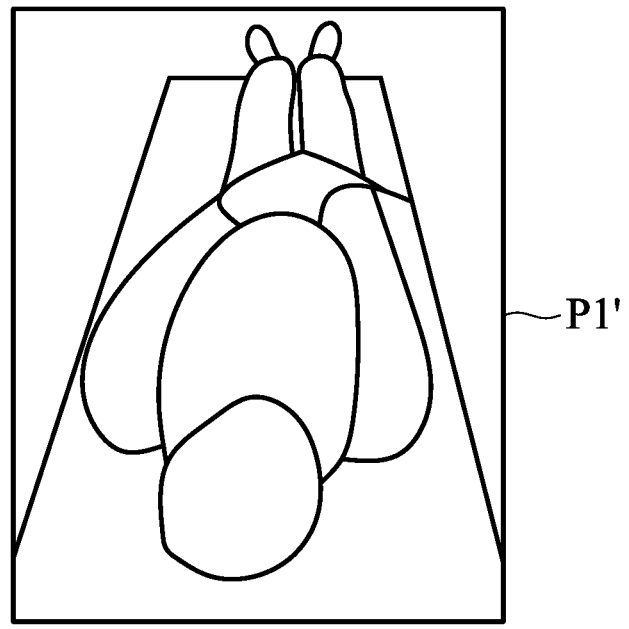
FIG. 3B is a schematic of executing a secondary differentiation on the sketch of the image according to an embodiment of the invention.

FIG. 3A is a schematic of an image P1 according to an embodiment of the invention. As shown in the figure, the image P1 mainly includes the user and the bed in which the user sleeps (which is the ROI). FIG. 3B is a schematic of executing a secondary differentiation on the sketch of the image according to an embodiment of the invention. In one embodiment, the secondary differentiation is utilized by the processor 200 to detect the user sketch. In other words, the processor performs the differentiation on the user sketch more than two times. Specifically, the secondary differentiation is utilized to obtain obvious edge features of the user in order to detect the user sketch (such as the image P1' of FIG. 3B).

In another embodiment, the primary differentiation or the edge detection algorithm (such as the Sobel algorithm) is utilized by the processor 200 to obtain the detailed features of the sketch and edge. In addition, after obtaining the image P1' of the user sketch, the processor 200 can perform a principal component analysis (PCA). PCA is a technique to analyze and simplify the database, reduce the degree of database, and maintain the database to contribute the greatest feature for the variables. In one embodiment, the processor 200 utilizes a PCA in association with the feature parameters such as the sketch, figure, body, or limbs of the user to analyze the body orientation of the user and the sleeping direction in the ROI. By utilizing the PCA, the body orientation of the user (which is the direction of the user on the bed) could be acquired to solve the problem of a distorted figure of the user.

Figure 4A:
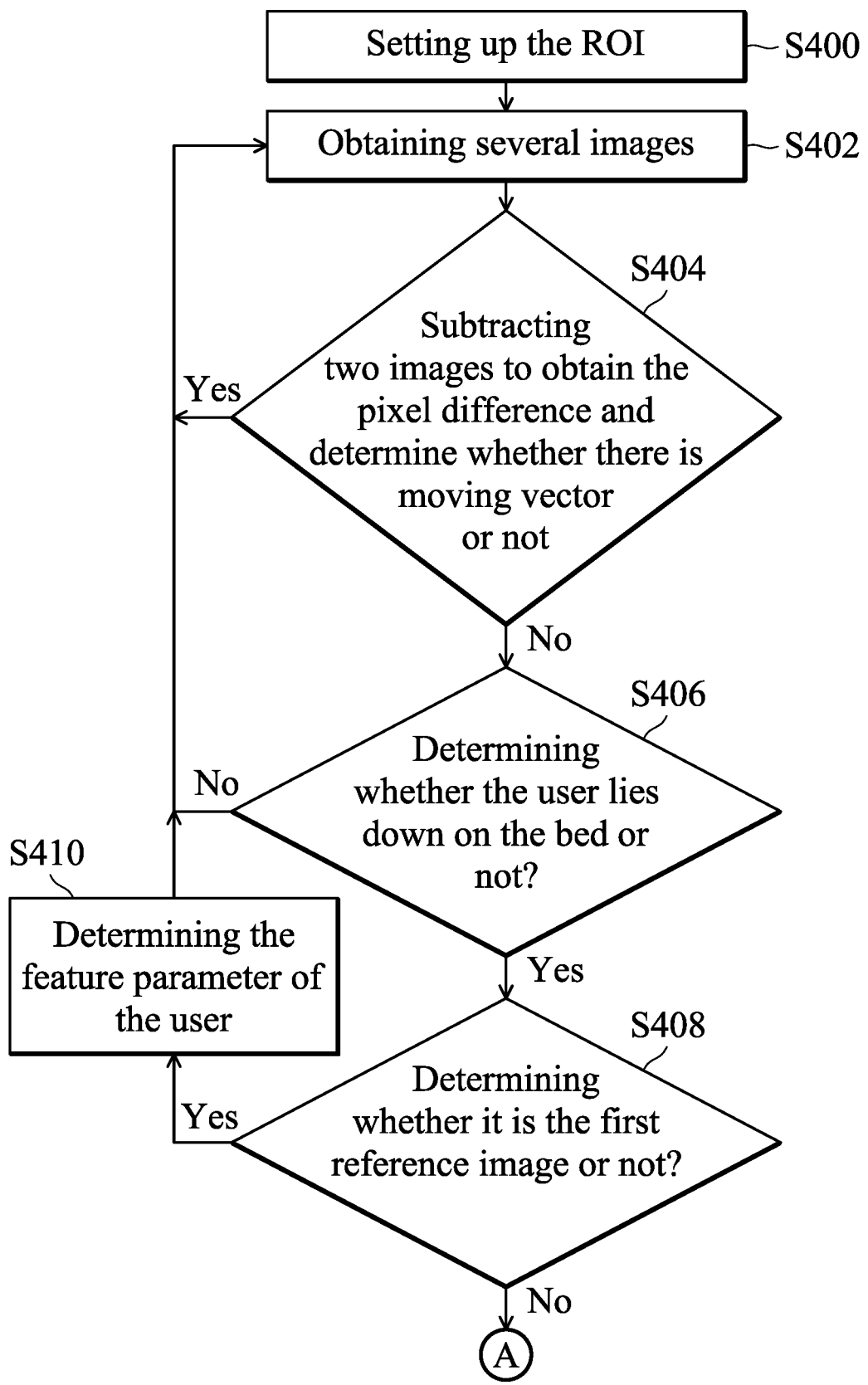
FIGS. 4A, 4B and 4C are a flow chart of an image detection method according to another embodiment of the invention.
Figure 4B:
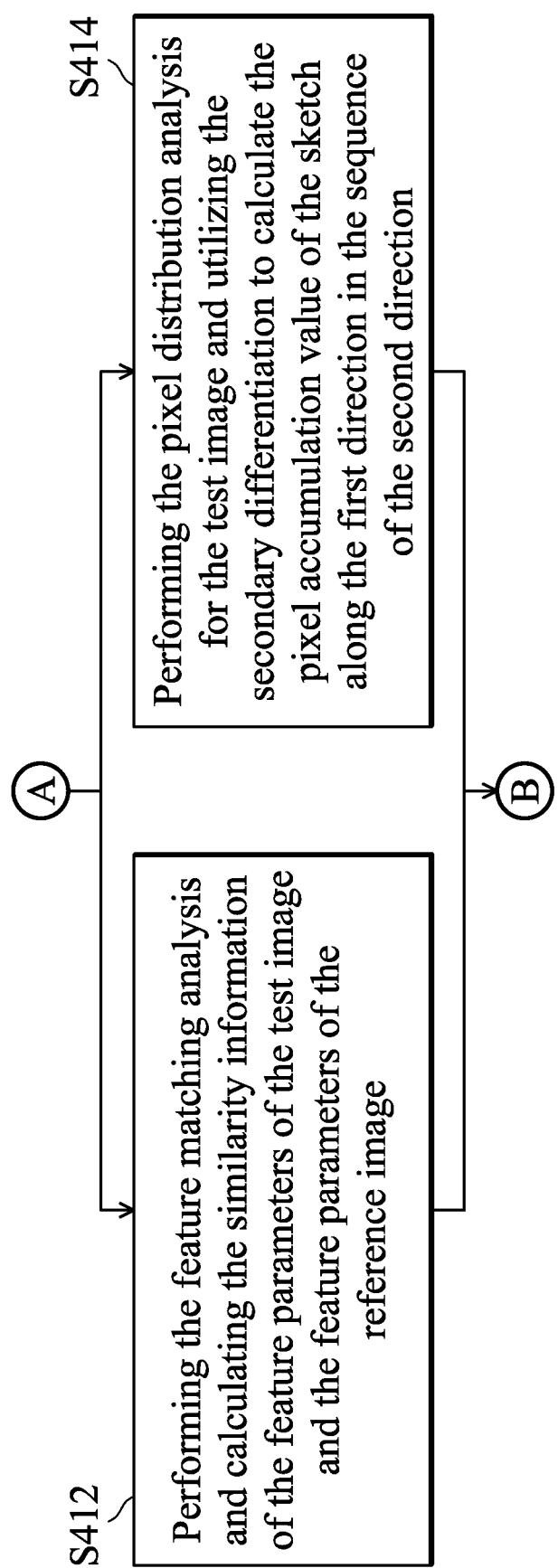
Figure 4C:
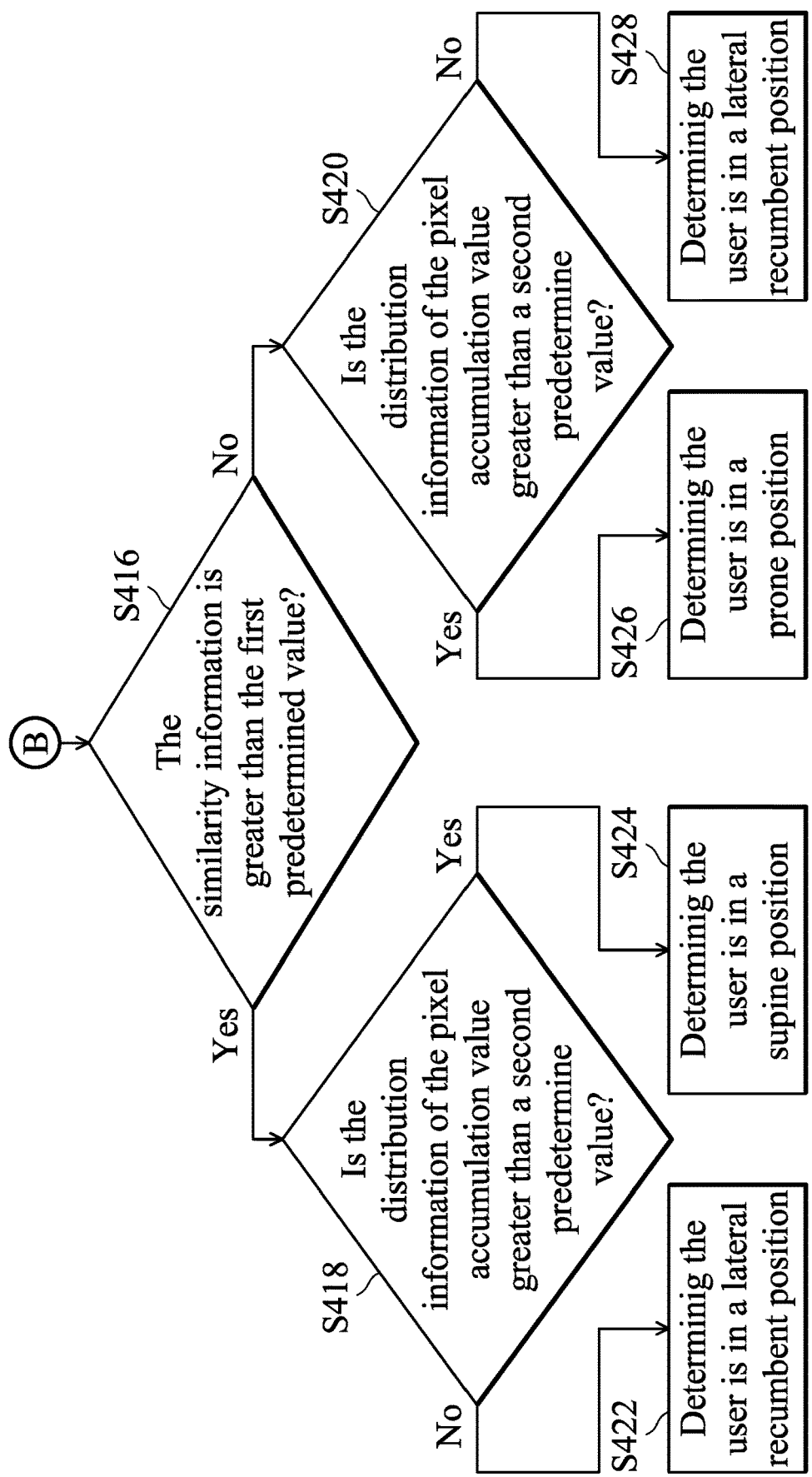

FIGS. 4A, 4B and 4C are a flow chart of an image detection method according to another embodiment of the invention. In step S400, the ROI is set up by the processor 200. In step S402, a plurality of images are obtained by the sensor 500. Afterwards, in step S404, two images are subtracted by the processor 200 to obtain the pixel difference in order to determine whether there is moving vector or not. When the electric signals of several images are received by the processor 200, various optical parameters such as the pixel, the resolution, and the color saturation could be extracted.

In one embodiment, the processor 200 subtracts the successive first image and second image to obtain the pixel difference, and defines the pixel difference as the moving vector. If the pixel difference is greater than a predetermined value, it means there is a moving vector, and the processor 200 determines that the user is in an active state rather than a motionless state. If the pixel difference is less than or equal to the predetermined value, it means there is no moving vector, and the processor 200 determines that the user is in a motionless state. For example, the predetermined value is 200. The value is for illustration, not for limiting the present invention. Specifically, the predetermined value could be adjusted based on the user environment and the need for the processor 200 to process an image.

In step S404, if the processor 200 determines there is a moving vector, step S402 will be executed again. In other words, the processor 200 will abandon the first image and obtain the third image, and compare the second image with the third image to determine whether there is a moving vector or not. If the processor 200 determines that there is no moving vector, step S406 will be executed to determine whether the user is lying down in the image or not. Therefore, by utilizing this method, a first reference image can be found in which the user has stopped moving and is lying still.

Specifically, in step S406, the algorithm (such as an OpenCV algorithm) or the classifier (such as an SVM classifier) for detecting body features is utilized by the processor 200. The body features, such as the sketch, figure, or skin color of the user, are utilized to determine whether the user is lying down within the image or not. If there is no body feature within the image, the processor 200 determines that the user is not lying down on the bed (or the ROI), and step S402 will be executed again. If there is a body feature within the image, the processor 200 determines that the user is lying down on the bed, and step S408 will be executed.

In step S408, the processor 200 determines whether the image is the first reference image or not. According to steps S402 to S408, if the processor 200 determines that the image does not have a moving vector and the user is lying down on the bed, it means that the image is the first reference image. Afterwards, step S410 is executed and the processor 200 determines feature parameters about the user. For example, a Hessian Matrix or Gabor Filter is executed to make the determination, but it is not limited thereto. The processor 200 utilizes a Hessian Matrix or Gabor Filter to extract the skin texture of the user to record the current state of the user. The above feature parameter includes any one of the limbs, any one of the facial features, the body of the user, or the specific figure of the clothing worn by the user.

In addition, if the processor 200 determines that the image is not the first reference image, the feature matching analysis of step S412 and the pixel distribution analysis of step S414 will be executed. In step S412, the processor 200 performs the feature matching analysis on the test image to calculate the similarity information of the feature parameters of the test image and the feature parameters of the reference image. In step S414, the processor 200 performs the pixel distribution analysis on the test image and utilizes the secondary differentiation to calculate the pixel accumulation value of the sketch along the first direction in the sequence of the second direction. For example, the second direction extends from the left side of the user to the right side of the user. The definition of the second direction is for illustration, not for limiting the present invention. Afterwards, the processor 200 determines the sleeping posture of the user according to the feature matching analysis of step S412 and the pixel distribution analysis of step S414.

Figure 5A:
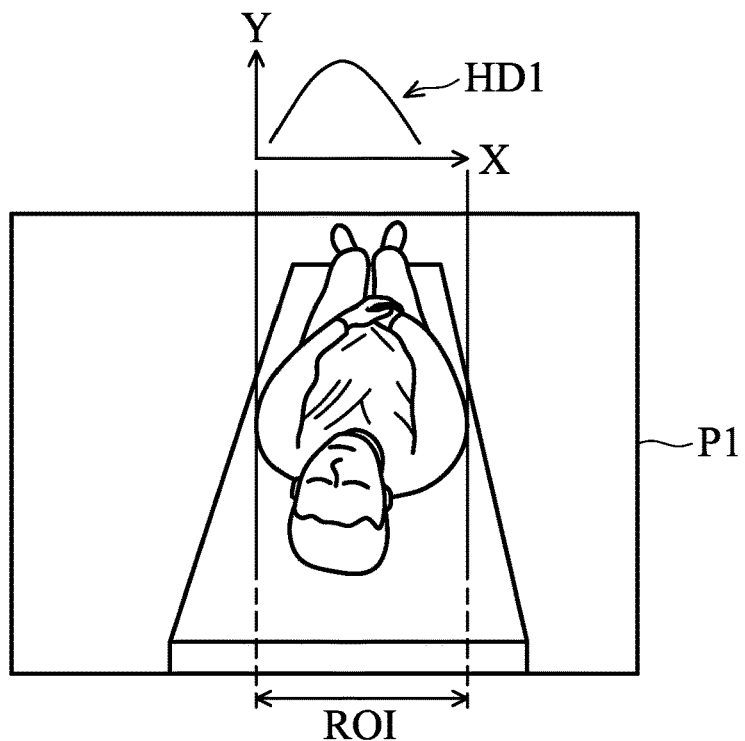
FIG. 5A is a schematic of calculating the user pixel distribution information of the pixel accumulation value according to an embodiment of the invention.
Figure 5B:
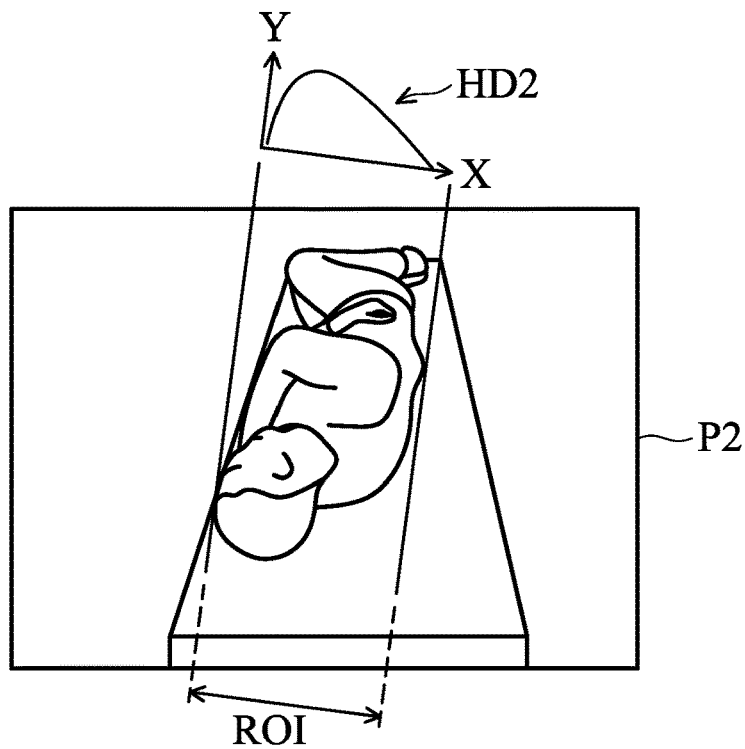
FIG. 5B is a schematic of calculating the user pixel distribution information of the pixel accumulation value according to another embodiment of the invention.

Specifically, during the pixel distribution analysis of step S414, the processor 200 performs a pixel distribution analysis on the test image to calculate the pixel accumulation value of the sketch along the first direction in the sequence of the second direction. The first direction extends from the head of the user to the foot of the user, and the second direction is different from the first direction. In one embodiment, the second direction is not parallel to the first direction. In another embodiment, the second direction is perpendicular to the first direction, which is not limited by the present invention. FIGS. 5A and 5B are schematics of calculating the user pixel distribution information of the pixel accumulation value according to an embodiment of the invention. As shown in the figures, images P1 and P2 both include the user and the ROI, which is the resting location of the user. The Y axis is the first direction which extends from the head of the user to the foot of the user, and the X axis is the second direction. Afterwards, the processor 200 calculates the pixel accumulation value on the Y axis, and compiles statistics for the distribution tendency for each pixel accumulation value on the X axis in order to obtain statistical diagrams HD1 and HD2.

Therefore, it could be realized that the pixel accumulation value is proportional to the weight of the body distribution. As shown in FIG. 5A, because the user in image P1 is lying on his or her back, the distribution of the statistical diagram HD1 is more symmetrical. In other words, the pixel accumulation value of the central portion of the body is high, and the pixel accumulation value of the side portion of the body is low. In the embodiment of FIG. 5B, because the user in image P2 is lying on his or her side in a lateral recumbent position, the distribution of the statistical diagram HD2 is less symmetrical, which tends to indicate that the user is in a lateral recumbent position. In other words, as for the statistical diagram HD2, there is higher pixel accumulation value on the side on which the user is lying. It should be noted that, in the embodiment of FIG. 5B, the side on which the user is lying results in a change of the body axis. Therefore, the processor 200 could utilize the PCA to obtain the body direction of the user, which is the direction in which the user is lying on the bed, and the problem of lying crooked can be solved.

In addition, it should be noted that the processor 200 could execute the feature matching analysis of step S412 and the pixel distribution analysis of step S414 simultaneously. In one embodiment, the processor 200 executes the feature matching analysis of step S412, then executes the pixel distribution analysis of step S414. In another embodiment, the processor 200 executes the pixel distribution analysis of step S414, then executes the feature matching analysis of step S412, which is not limited by the present invention.

Afterwards, in step S416, the processor 200 determines whether the similarity information is greater than the first predetermined value. For example, the processor 200 determines whether the similarity information of the feature parameters of the test image and the feature parameters of the reference image is greater than 80%. The threshold value of 80% is used for illustration, not for limitation. The above threshold value could be adjusted by the processor 200 based on the user's environment and the image processing requirements. If yes, step S418 will be executed. If not, step S420 will be executed.

During steps S418 and S420, the processor 200 determines whether the user pixel distribution information of the above pixel accumulation value is greater than a second predetermined value or not. When the value of the user pixel distribution information is higher, it indicates that the distribution is more symmetrical. In step S418, if the user pixel distribution information of the above pixel accumulation value is not greater than a second predetermined value, step S422 will be executed and the processor 200 determines that the user is in a lateral recumbent position. If the user pixel distribution information of the above pixel accumulation value is greater than the second predetermined value, step S424 will be executed and the processor 200 determines that the user is in the supine position.

Furthermore, in step S420, if the user pixel distribution information of the above pixel accumulation value is greater than the second predetermined value, step S426 will be executed and the processor 200 determines that the user is in the prone position. If the user pixel distribution information of the above pixel accumulation value is not greater than the second predetermined value, step S428 will be executed and the processor 200 determines that the user is in a lateral recumbent position.

In embodiments of the present invention, a body feature such as the trunk or a limb of user is selected as the feature parameter for matching and analysis, and the pixel accumulation value of the user sketch is calculated to perform the pixel distribution analysis. Even though the body of the user is covered by bedding or other cloth, the sleeping posture of the user can still be determined based on the change of the covered figure and sketch. Even if the face of the user cannot be identified, the sleeping posture of the user can be precisely determined based on the above body features in order to help take care of the user.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having the same name (but for use of the ordinal term) to distinguish the claim elements.

While the invention has been described by way of example and in terms of the preferred embodiments, it should be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An image detection method for determining a posture of a user, comprising:
   obtaining a reference image of a user in a region of interest (ROI);
   obtaining a test image of the user in the ROI;
   executing a feature matching analysis on a feature parameter of the test image and a feature parameter of the reference image to obtain user similarity information of the test image and the reference image;
   executing a pixel distribution analysis for the test image to obtain user pixel distribution information; and
   determining the posture of the user based on the user similarity information and the user pixel distribution information,
   wherein the similarity information of the feature parameter of the test image and the feature parameter of the reference image is calculated to determine whether it is greater than a first predetermined value or not, and the pixel distribution analysis is utilized to calculate a pixel accumulation value of a user outline along the first direction respectively based on a sequence of a second direction, and whether the user pixel distribution information of the pixel accumulation value is greater than a second predetermined value or not, and
   when the similarity information is greater than the first predetermined value and the user pixel distribution information is greater than the second predetermined value, it is determined that the user is in a supine position; and
   when the similarity information is greater than the first predetermined value and the user pixel distribution information is smaller than or equal to the second predetermined value, it is determined that the user is in a lateral recumbent position.

2. The image detection method as claimed in claim 1, wherein the pixel distribution analysis is utilized to accumulate pixels for the user outline of the test image along a first direction to obtain the user pixel distribution information.

3. The image detection method as claimed in claim 1, wherein the test image is different from the reference image.

4. The image detection method as claimed in claim 1, further comprising:
   determining the reference image from a plurality of images captured by an image sensor based on whether a pixel difference derived from subtracting two successive images among the images captured by the image sensor is smaller than a predetermined value or not.

5. The image detection method as claimed in claim 1, wherein the ROI is a bed on which the user is lying, and the feature parameter comprises any one of limbs, any one of facial features, trunk of the user, or a specific pattern of an article of clothing worn by the user.

6. The image detection method as claimed in claim 1, wherein:
   when the similarity information is smaller than or equal to the first predetermined value and the user pixel distribution information is greater than the second predetermined value, it is determined that the user is in a prone position; and
   when the similarity information is smaller than the first predetermined value and the user pixel distribution information is smaller than or equal to the second predetermined value, it is determined that the user is in a lateral recumbent position.

7. The image detection method as claimed in claim 1, wherein the first direction extends from head of the user to foot of the user, and the second direction is different from the first direction.

8. The image detection method as claimed in claim 7, wherein the second direction is vertical to the first direction.

9. An image detection device, comprising:
   a sensor, configured to detect a test image and a reference image of a user in a region of interest (ROI); and
   a processor, comprising:
   a feature matching module, configured to execute a feature matching analysis of a feature parameter of the test image and a feature parameter of the reference image to obtain user similarity information of the test image and the reference image, and execute a pixel distribution analysis for the test image to obtain user pixel distribution information; and
   a determination module, configured to determine a posture of the user based on the user similarity information and the user pixel distribution information,
   wherein the processor calculates the similarity information of the feature parameter of the test image and the feature parameter of the reference image to determine whether it is greater than a first predetermined value or not, and the pixel distribution analysis is utilized to calculate a pixel accumulation value of a user outline along the first direction respectively based on a sequence of a second direction, and the processor calculates whether the user pixel distribution information of the pixel accumulation value is greater than a second predetermined value or not,
   wherein when the similarity information is greater than the first predetermined value and the user pixel distribution information is greater than the second predetermined value, it is determined that the user is in a supine position,
   wherein when the similarity information is greater than the first predetermined value and the user pixel distribution information is smaller than or equal to the second predetermined value, it is determined that the user is in a lateral recumbent position.

10. The image detection device as claimed in claim 9, wherein the pixel distribution analysis is utilized to accumulate pixels for the user outline of the test image along a first direction to obtain the user pixel distribution information.

11. The image detection device as claimed in claim 9, wherein:
- when the similarity information is smaller than or equal to the first predetermined value and the user pixel distribution information is greater than the second predetermined value, it is determined that the user is in a prone position; and
- when the similarity information is smaller than the first predetermined value and the user pixel distribution information is smaller than or equal to the second predetermined value, it is determined that the user is in a lateral recumbent position.

12. The image detection device as claimed in claim 9, wherein the first direction extends from the head of the user to the foot of the user, and the second direction is different from the first direction.

13. The image detection device as claimed in claim 12, wherein the second direction is vertical to the first direction.

* * * * *